United States Patent
Walter (10) Patent No.: US 9,541,473 B2
(45) Date of Patent: Jan. 10, 2017

(54) MICROTOME HAVING A PIEZOELECTRIC LINEAR ACTUATOR

(71) Applicant: Leica Biosystems Nussloch GmbH, Nussloch (DE)

(72) Inventor: Roland Walter, Reilingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 135 days.

(21) Appl. No.: 13/926,599

(22) Filed: Jun. 25, 2013

(65) Prior Publication Data
US 2014/0026727 A1    Jan. 30, 2014

(30) Foreign Application Priority Data

Jul. 27, 2012 (DE) .......... 10 2012 106 846

(51) Int. Cl.
*G01N 1/06* (2006.01)

(52) U.S. Cl.
CPC ........... *G01N 1/06* (2013.01); *G01N 2001/065* (2013.01); *Y10T 83/162* (2015.04); *Y10T 83/6515* (2015.04); *Y10T 83/6536* (2015.04)

(58) Field of Classification Search
CPC ...... G01N 1/04; G01N 1/06; G01N 2001/065; G01N 2001/066; G01N 2001/061; G01N 2001/068; Y10S 83/9155
USPC ........................................ 83/915.5
See application file for complete search history.

(56) References Cited

U.S. PATENT DOCUMENTS

| | | | | | |
|---|---|---|---|---|---|
| 3,845,659 | A * | 11/1974 | Wikefeldt | .......... | B23Q 17/0976 73/862.06 |
| 4,377,958 | A * | 3/1983 | Leighton | .................. | G01N 1/06 83/410.7 |
| 5,282,404 | A * | 2/1994 | Leighton et al. | ................. | 83/13 |
| 5,535,654 | A * | 7/1996 | Niesporek | ................ | G01N 1/06 200/47 |
| 5,782,572 | A * | 7/1998 | Thiem | ....................... | G01N 1/06 248/288.31 |
| 6,586,862 | B1 * | 7/2003 | Cselle | .......................... | 310/328 |
| 7,080,583 | B2 * | 7/2006 | Lihl et al. | ........................ | 83/13 |
| 7,503,248 | B2 * | 3/2009 | Studer | ............................ | 83/703 |
| 7,802,507 | B2 * | 9/2010 | Ito | ............................ | G01N 1/06 83/169 |
| 8,051,760 | B2 * | 11/2011 | Walter | ..................... | G01N 1/06 83/713 |
| 8,246,905 | B2 * | 8/2012 | Teppke | ..................... | A61L 2/20 422/1 |
| 2004/0107807 | A1 * | 6/2004 | Studer | ............................. | 83/13 |
| 2006/0248997 | A1 * | 11/2006 | Studer | ............................ | 83/427 |

(Continued)

FOREIGN PATENT DOCUMENTS

DE  33 313 A1  11/1964
DE  19 22 739 U  11/1970

(Continued)

*Primary Examiner* — Jason Daniel Prone
*Assistant Examiner* — Richard Crosby, Jr.
(74) *Attorney, Agent, or Firm* — Hodgson Russ LLP (57) ABSTRACT

The present invention relates to a microtome (10) for cutting thin sections, including a sample holder (12), a cutting unit (16), and a drive unit (16) for producing a feed movement between the sample holder (12) and the cutting unit (16) for setting the thickness of the sample sections. The drive unit (22) includes a piezoelectric linear actuator (50) for producing the feed movement.

16 Claims, 7 Drawing Sheets

(56) References Cited

U.S. PATENT DOCUMENTS

| | | | | |
|---|---|---|---|---|
| 2007/0204734 | A1* | 9/2007 | Ito et al. .......................... | 83/170 |
| 2010/0058913 | A1* | 3/2010 | Walter ............................ | 83/648 |
| 2011/0252935 | A1* | 10/2011 | Welsh .............................. | 83/37 |

FOREIGN PATENT DOCUMENTS

| | | |
|---|---|---|
| DE | 36 03 278 C1 | 9/1986 |
| DE | 38 20 085 C1 | 7/1989 |
| DE | 3820085 C1 * | 7/1989 |
| DE | 199 11 163 C1 | 7/2000 |
| DE | 101 54 843 A1 | 5/2003 |
| DE | 102 10 408 B4 | 9/2003 |
| DE | 102 18 927 C1 | 11/2003 |
| DE | 10 2008 016 165 B4 | 10/2009 |
| DE | 10 2009 006 386 B4 | 8/2010 |
| DE | 10 2010 046 498 B3 | 12/2011 |
| JP | 10104131 A | 4/1998 |
| SE | 8605532 A | 6/1988 |

\* cited by examiner

MICROTOME HAVING A PIEZOELECTRIC LINEAR ACTUATOR

CROSS REFERENCE TO RELATED APPLICATIONS

This application claims priority of German patent application number 10 2012 106 846.1 filed Jul. 27, 2012, the entire disclosure of which is incorporated by reference herein.

FIELD OF THE INVENTION

The present invention relates to a microtome for cutting thin sections, including a sample holder for receiving a sample to be microtomed and a cutting unit for cutting the sample. Also provided is a feed motion drive unit for producing a feed movement between the sample holder and the cutting unit for setting the thickness of the thin sections.

BACKGROUND OF THE INVENTION

In order to perform the microtoming operation, the samples (e.g., tissue samples) are clamped in the sample holder, which is caused by a cutting motion drive unit to perform a reciprocating movement relative to the cutting unit, thereby cutting the sample. After such a reciprocating movement; i.e., after a thin section is cut from the sample, the distance between the sample holder and the cutting unit must be reduced by the thickness of the next thin section. This generally horizontal movement is referred to as "feed movement." The feed movement and the reciprocating movement are in particular orthogonal to each other, the reciprocating movement being vertical and the feed movement being horizontal.

Microtomes are known where the feed movement is produced purely mechanically via free-wheeling lever and/or screw and nut systems. Also known are microtomes where the feed is accomplished electromechanically using stepper motor and screw and nut systems. A microtome including a linear motor for moving the sample holder and the cutting unit relative to each other is known from document DE 10 2008 016165 B5.

The disadvantage of the known microtomes is that the resolution; i.e, the minimum adjustable thickness of the thin sections, is limited by the screw pitch of the screw and nut systems and the minimum step resolution of the stepper motor. To be able to achieve very small steps, and thus very thin sections, it is necessary, in particular, to use very complex designs with expensive screw and nut components. Such designs also require complex, cost-intensive bearing arrangements and are associated with high space requirements and high weight. Moreover, such expensive designs having high-resolution screw and nut components and corresponding motors have the disadvantage that they do not allow rapid movement of the sample holder relative to the cutting unit and, therefore, the feed can be effected only very slowly during sample change in the so-called coarse feed mode of the microtome.

Patent Publications DE 38 20 085 C1, DD 33 313 A1, DE 19 22 739 U, U.S. Pat. No. 5,282,404 A, U.S. Pat. No. 4,377,958 A and DE 10 2009 006 386 B4 describe microtomes in which the object holder is rigidly connected to piezoelectric elements, and the feed movement of the object holder is produced by a change in length of the piezoelectric elements.

Further microtomes are known from documents DE 199 11 163 C1, DE 10 2010 046 498 B3, DE 102 18 927 C1, DE 102 10 408 B4, DE 101 54 843 A1 and DE 36 03 278 C1.

SUMMARY OF THE INVENTION

It is an object of the present invention to provide a microtome for cutting thin sections, which allows very thin sections to be cut with high accuracy and enables precise control of the feed movement.

This object is achieved by a microtome having the features of claim 1. Advantageous refinements are recited in the dependent claims.

In accordance with the present invention, the feed motion drive unit includes a piezoelectric linear actuator for producing the feed movement. The piezoelectric linear actuator includes a stationary stator and a runner which is connected to the stator via at least one piezoelectric element. The piezoelectric element is adapted to be capable of linearly moving the runner relative to the stator. Here, the piezoelectric element is fixedly attached to the stator, and the runner is movable relative to the piezoelectric element. The advantage of such piezoelectric linear actuators is that they have a resolution of a few nanometers, which makes it possible to obtain a step size of a few nanometers. Thus, a significantly higher resolution can be achieved than with known microtomes and screw and nut systems. This makes it possible in particular to dispense with expensive screw and nut systems and corresponding bearing arrangements.

Since such piezoelectric linear actuators are designed as direct drives, the number of required components is markedly reduced, which enables a space-saving microtome design of low weight. This makes it possible to obtain very precise microtomes of compact design and, in particular, to dispense with a stepper motor and a corresponding clutch.

Furthermore, piezoelectric linear actuators not only allow a very accurate feed movement in small steps, but also make it possible to achieve high speeds of movement, so that, for example, during sample change, the sample holder and the cutting unit may be rapidly moved away from or toward each other, which allows sample changes to be performed as quickly as possible.

Examples of materials that may be used for the piezoelectric element include, in particular, piezoelectric ceramics or piezoelectric crystals.

Further it is advantageous to provide a control unit which energizes the piezoelectric element in such a way that it moves the runner linearly according to a preset sequence of movements. In this way, it is achieved that the feed movement between the sample holder and the cutting unit can be controlled very precisely in a simple manner. In particular, the control unit controls the piezoelectric linear actuator in such a way that each time a reciprocating movement for cutting a thin section is completed, the piezoelectric linear actuator moves the sample holder relative to the cutting unit through a preset distance which corresponds in particular to the desired thickness of the thin sections.

In a particularly preferred embodiment, the cutting unit is stationary and the sample holder is movable relative to the cutting unit by the feed motion drive unit. In an alternative embodiment of the present invention, the sample holder may be stationary and the cutting unit may be moved relative thereto. Alternatively, both the cutting unit and the sample holder may be mounted such that they are movable.

The sample holder is in particular fixedly connected to the runner of the piezoelectric linear actuator, so that when the runner is moved, the sample holder is moved along therewith, thus producing the feed movement.

The sample holder is preferably attached to a carriage which is mounted on a guide member such that it is movable in the direction of a longitudinal axis of this guide member. The runner of the piezoelectric linear actuator is attached to the carriage, and the stator of the piezoelectric linear actuator is attached to the guide member. Thus, when the runner is moved relative to the stator, the carriage is also moved relative to the guide member, thereby also moving the sample holder mounted on the carriage. This provides simple and reliable guidance for the feed movement.

In an alternative embodiment of the present invention, the stator may be mounted on the carriage and the runner may be mounted on the guide member. In both embodiments, the guide member may preferably be in the form of a rail, so that reliable guidance of the carriage is achieved.

In a particularly preferred embodiment, the guide member is mounted on a further carriage which can be moved by a further drive unit, referred to herein as a cutting motion drive unit. The further carriage can be moved by the cutting motion drive unit in particular in such a way that the cutting motion drive unit can cause the sample holder to perform a reciprocating movement relative to the cutting unit to cut the samples to be microtomed. For this purpose, the further carriage is in particular attached to a further rail or a differently configured further guide member, the longitudinal axes of the one rail and the longitudinal axes of the further rail being in particular orthogonal to each other, so that the reciprocating cutting movement and the feed movement are also orthogonal to each other.

The cutting motion drive unit is in particular in the form of a motor by which a rotational movement of a handwheel detected by an encoder is converted into a corresponding reciprocating movement. Alternatively, it is also possible to provide a purely mechanical coupling between the handwheel and the further carriage for producing the reciprocating movement.

It is also advantageous to provide a sensor for detecting the travel of the piezoelectric linear actuator. This makes it possible to precisely track the instantaneous position of the runner relative to the stator; i.e., the distance currently traveled. Unlike in a drive implemented by a stepper motor, such a sensor is necessary because the travel cannot be detected simply by counting the number of defined steps.

The sensor includes in particular a linear encoder attached to the guide member and a scale provided on the carriage. Using the linear encoder, the steps of the scale are counted, thus allowing determination of the distance traveled. The scale may be in the form of, for example, a graduation or a rule provided on the carriage. Alternatively, the linear encoder may be attached to the carriage and the linear scale may be provided on the guide member.

It is also advantageous to provide a control unit for controlling the piezoelectric linear actuator. After a thin section is cut, this control unit controls the piezoelectric linear actuator in such a way that the piezoelectric linear actuator performs a feed movement through a preset distance. Thus, each time a thin section has been cut from the sample, the sample holder is advanced through said preset distance, whereupon a new thin section can be cut off from the sample, the thickness of said section corresponding to said preset distance.

In a particularly preferred embodiment, the microtome includes an operator control unit which can be used to set this preset distance. Thus, the section thickness can be easily matched to the sample to be microtomed. The operator control can be used, for example, to select the desired section thickness from a large number of possible preset section thicknesses. Alternatively, the desired section thickness may also be freely input.

Additionally or alternatively, the operator control unit may also be used to set the speed at which the sample holder and the cutting element are moved relative to each other. This makes it possible, for example, to select a high speed for the sample change, whereas a low speed is used for the actual feed movement during the cutting of the samples.

The operator control unit may in particular be operated manually by a user. Alternatively, the preset distance and/or the speed may also be set using a computer coupled to the microtome via a data link.

BRIEF DESCRIPTION OF THE DRAWING VIEWS

Further features and advantages of the present invention will become apparent from the following description of exemplary embodiments thereof, taken in conjunction with the accompanying drawings, in which.

DETAILED DESCRIPTION OF THE INVENTION

Figure 1:
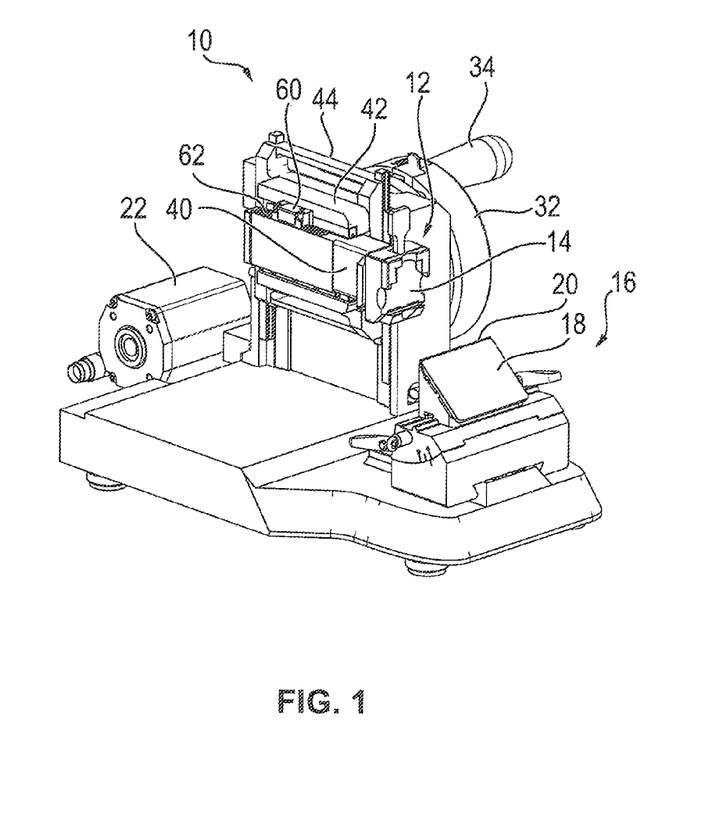
FIG. 1 is a schematic perspective view of a microtome.
Figure 2:
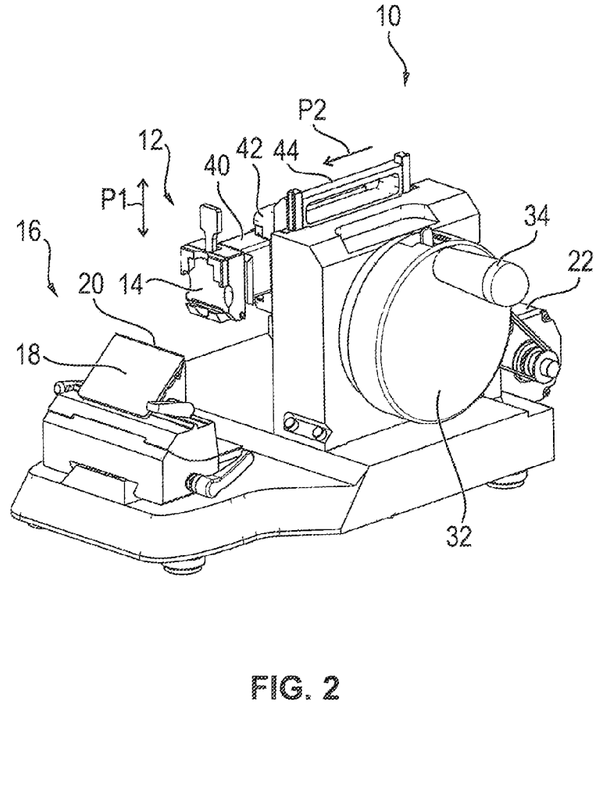
FIG. 2 is a further schematic perspective view of the microtome of FIG. 1.

FIGS. 1 and 2 are each schematic perspective views depicting a microtome 10 in greatly simplified form and showing only the components that are essential to the invention. For example, the housing has been omitted to allow viewing of the interior components.

Microtome 10 includes a sample holder 12 including a chuck 14 for holding a sample to be microtomed. Microtome 10 further has a cutting unit 16 including a blade holder 18 and a blade 20 received in blade holder 18 for cutting the sample.

Furthermore, microtome 10 includes a handwheel 32 having a handle 34. Rotational movement of handwheel 32 is detected by a rotary encoder (not shown). A control unit 23 (shown in FIG. 9) controls a cutting motion drive unit 22 according to the detected rotational movement of handwheel 32 in such a way that sample holder 12 performs a reciprocating movement in the direction of double-headed arrow P1 relative to stationary cutting unit 16, so that the sample is cut into thin sections by contact with blade 20. Each stroke produces one thin section.

In an alternative embodiment, handwheel 32 may also be mechanically coupled to sample holder 12, so that no cutting motion drive unit 22, in particular no motor, is needed for the reciprocating movement, but instead, the reciprocating movement is performed purely mechanically by rotating handwheel 32.

After a thin section is cut, sample holder 12 must be moved horizontally in the direction of arrow P2 toward cutting unit 16, so that a new thin section can be cut from the sample at the next stroke. This linear movement is referred to as "feed movement" or "feed." The distance through which sample holder 12 is moved in the direction of arrow P2 after each stroke is used, in particular, to set the thickness of the thin sections. Accordingly, the smaller the possible step size of the feed movement, the thinner the sections that can be cut.

Figure 3:
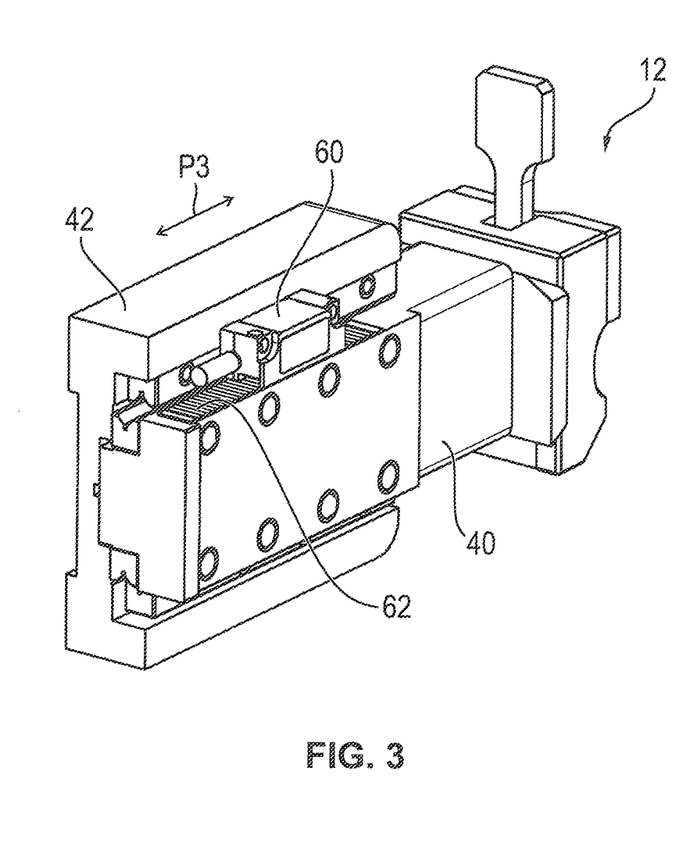
FIG. 3 is a schematic perspective view of a detail of the microtome shown in FIGS. 1 and 2.
Figure 4:
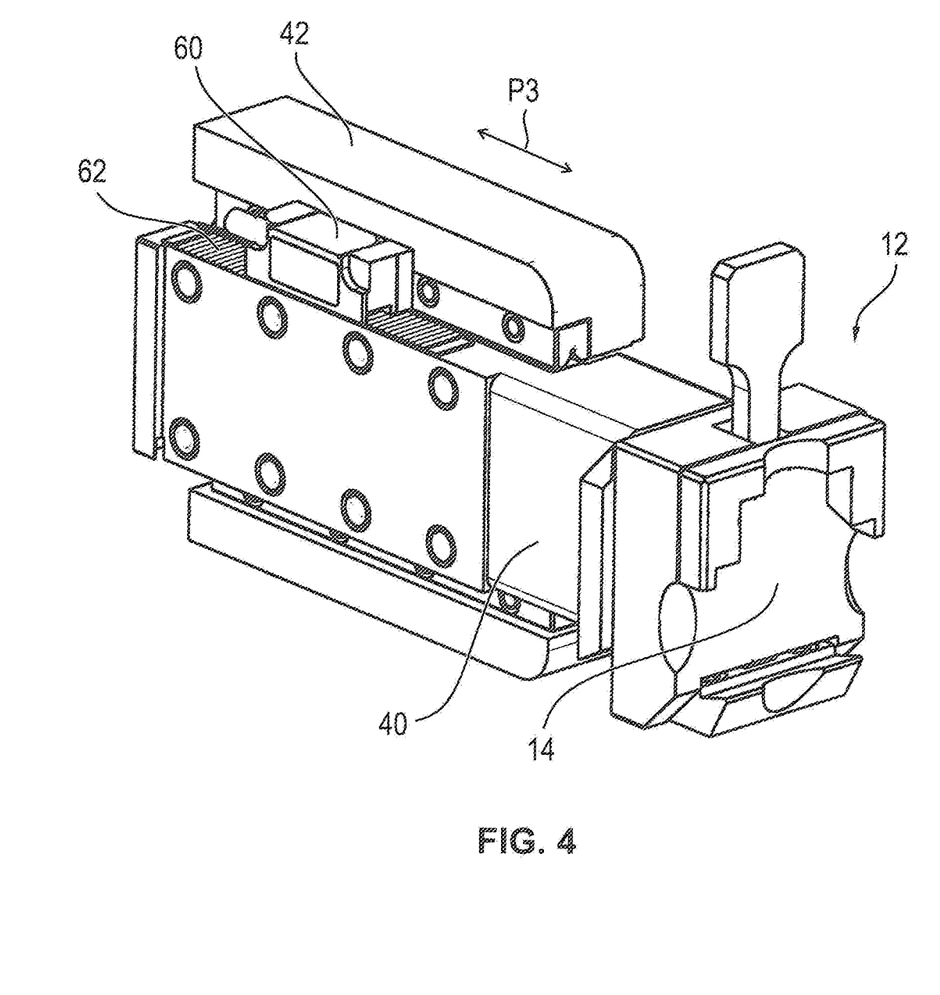
FIG. 4 is a further schematic perspective view of the detail of FIG. 3.
Figure 5:
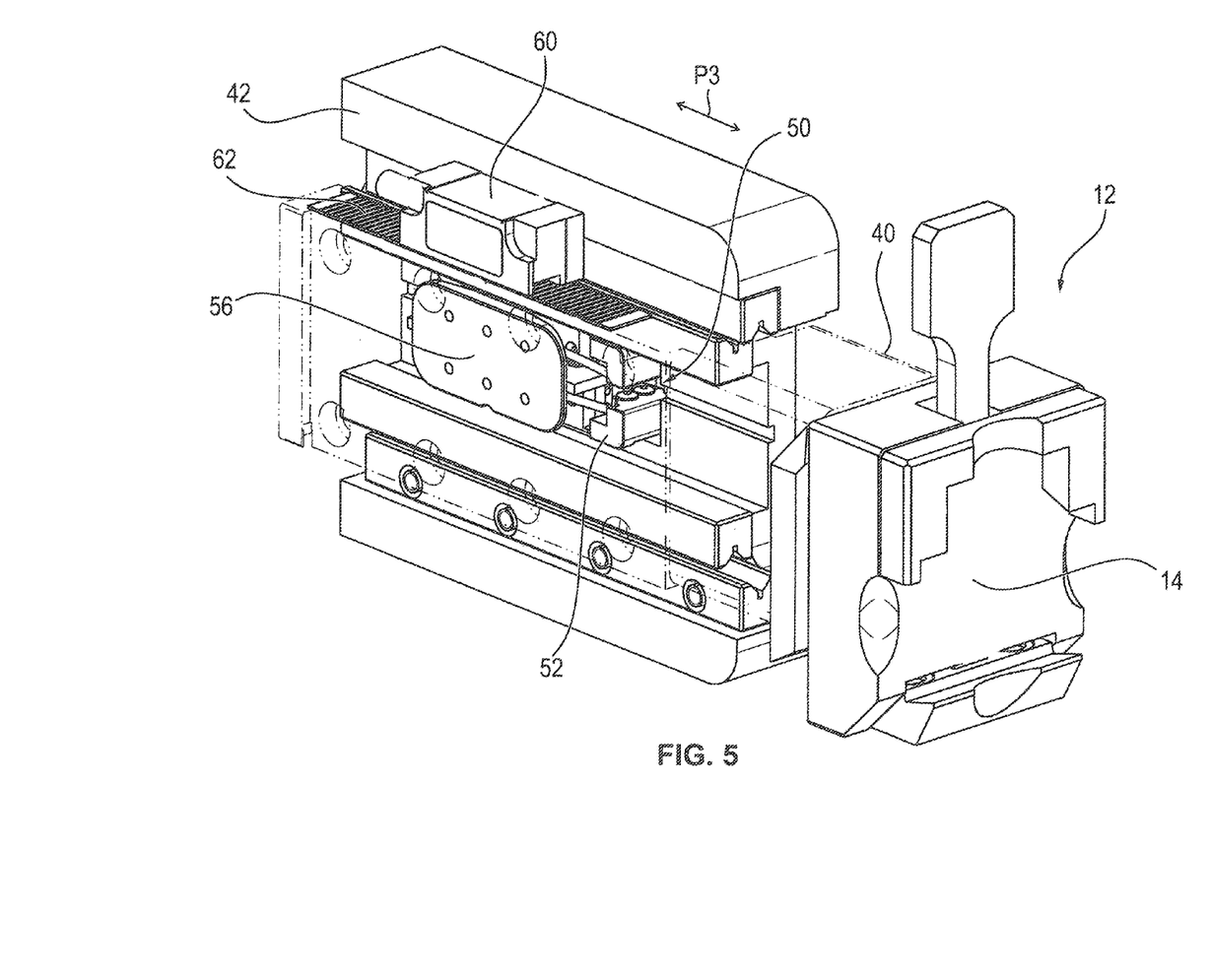
FIG. 5 is another schematic perspective view of the detail shown in FIGS. 3 and 4.
Figure 6:
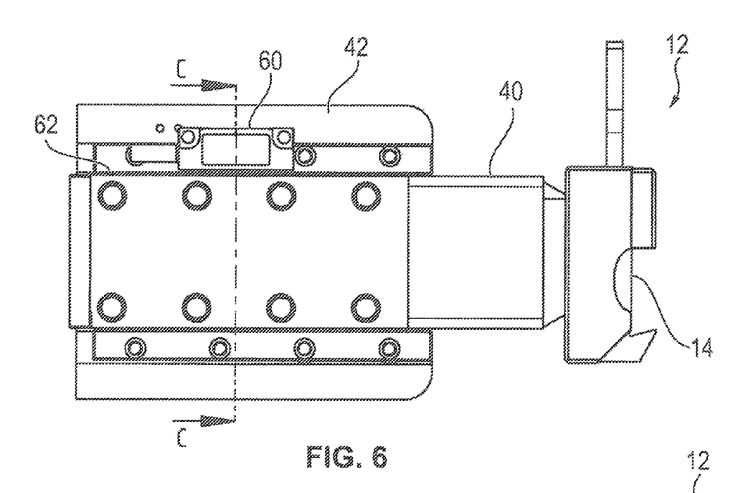
FIG. 6 is a side view of the detail shown in FIGS. 3 through 5.
Figure 7:
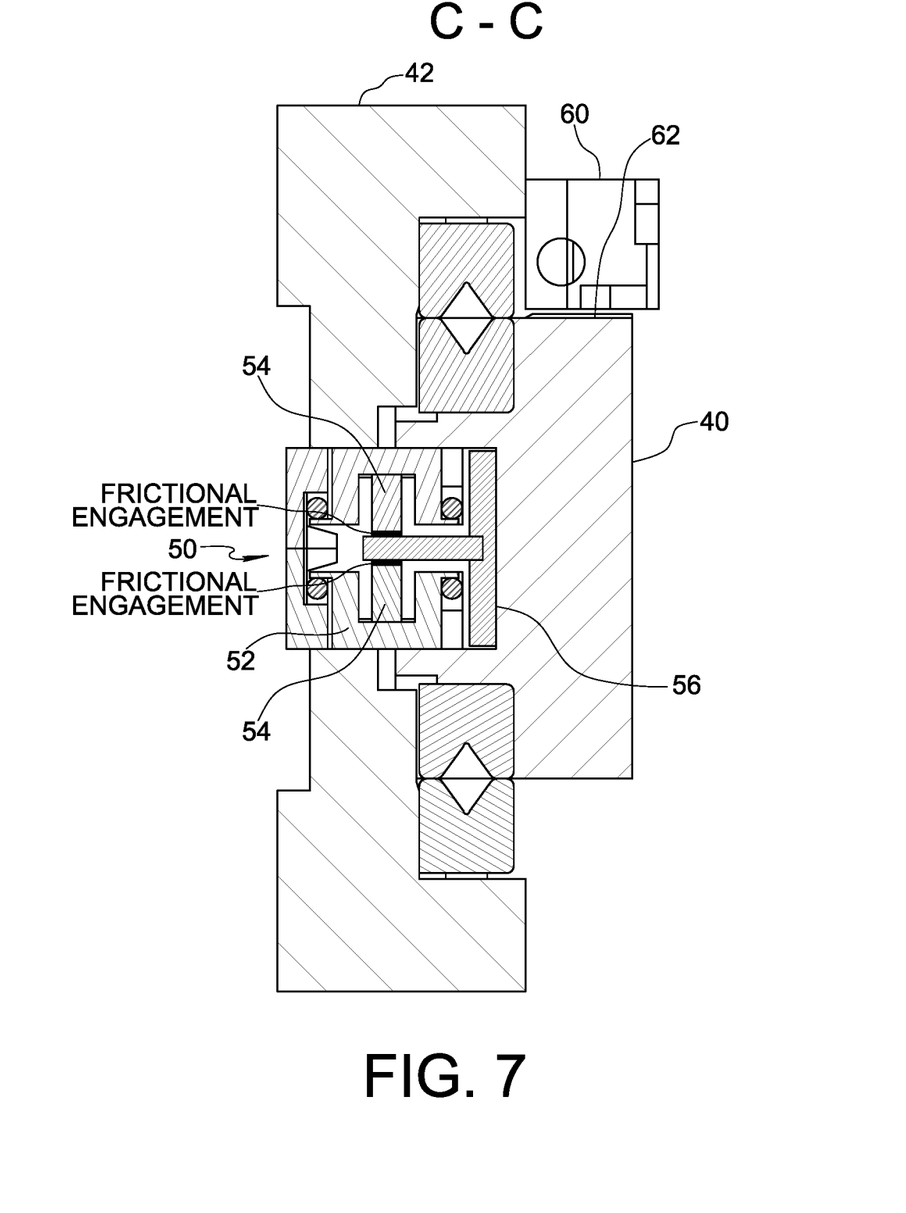
FIG. 7 is a sectional view of the detail shown in FIGS. 3 through 6.
Figure 8:
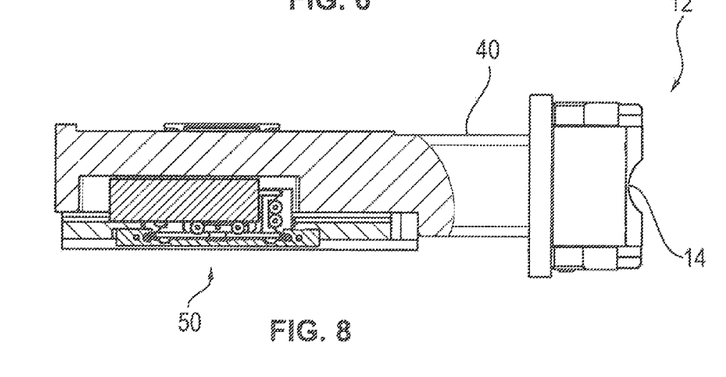
FIG. 8 is another, partially sectional view of the detail shown in FIGS. 3 through 7.

In accordance with the present invention, the feed movement is accomplished by a feed motion drive unit having a piezoelectric linear actuator. This feed motion drive unit is shown in detail in FIGS. 3 through 8. FIGS. 3 through 5 are each schematic perspective views, with FIG. 6 being a side view, and FIGS. 7 and 8 being sectional views.

Sample holder 12 is fixedly mounted on a carriage 40 which is supported in a rail-type guide member 42 such that it is horizontally movable in the direction of double-headed arrow P3. This guide member 42 is in turn attached to a further carriage 44 which is movable vertically by cutting motion drive unit 22 in the direction of double-headed arrow P1, and thus performs the reciprocating movement for cutting the samples. Thus, the reciprocating movement of the further carriage 44 causes guide member 42 to correspondingly move vertically, so that sample holder 42, and thus also carriage 40 and sample holder 12, perform a corresponding reciprocating movement.

Piezoelectric linear actuator 50 includes a stator 52 and a runner 56 which is connected to stator 52 via at least one piezoelectric element 54. This piezoelectric element 54 is capable of linearly moving runner 56 relative to stator 52 in the direction of double-headed arrow P3.

Stator 52 is attached to guide member 42, whereas runner 56 is attached to carriage 40, so that when runner 56 is moved by piezoelectric element 54 relative to stator 52, carriage 40, and thus sample holder 12, are also moved relative to guide member 42 in the direction of double-headed arrow P3, thereby performing feed movement.

Here, piezoelectric element 54 is disposed stationary with respect to stator 52. When suitably energized, piezoelectric element 54 changes its shape in such a way that runner 56 is linearly moved in the direction of double-headed arrow P3 by its contact with piezoelectric element 54.

Examples of piezoelectric linear actuators that may be used are the "Piezo LEGS Caliper 20N" piezoelectric motor or the "Piezo LEGS LT2010A" piezoelectric motor produced by PiezoMotor Uppsala AB.

In comparison with known microtomes, where the feed movement is performed purely mechanically via screw and nut systems and/or electromechanically by means of stepper motors and corresponding screw and nut systems, the use of a linear actuator has the advantage of enabling a step size of a few nanometers. This provides a very high resolution, making it possible, on the one hand, to produce very thin sections and, on the other hand, to achieve the desired thickness with high accuracy.

Piezoelectric linear actuator 50 further has the advantage that it operates as a direct drive, which eliminates the need for a motor, a clutch and additional bearing elements, making it possible to achieve a simple, cost-effective and space-saving design. Thus, in particular, a microtome 10 can be manufactured that is compact and lightweight.

In addition, piezoelectric linear actuator 50 permits a large travel, allowing carriage 40 to be moved at high speed relative to guide member 42. Therefore, when microtome 10 is in the so-called coarse feed mode (e.g. during sample change), a large distance can be traveled in a short time, thus enabling rapid sample change.

Furthermore, there is provided an operator control unit 25 (shown in FIG. 9) which can be used to set the speed. The operator control unit 25 can in particular be used to select between coarse feed and fine feed. These modes each have different preset speeds associated therewith, the speed setting for coarse feed being significantly higher than that for fine feed.

Figure 9:
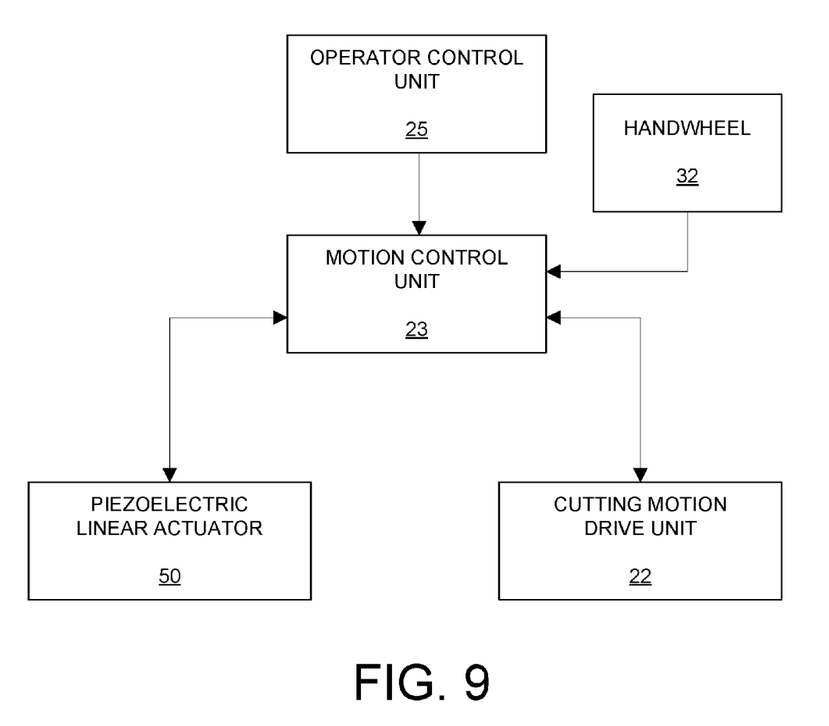
FIG. 9 is a schematic block diagram showing an operator control unit and a motion control unit of the microtome.

Furthermore, the operator control unit 25 can also be used in particular to set the desired section thickness. The control unit 23 then controls piezoelectric linear actuator 50 in such a way that after each stroke, it moves runner 56 toward cutting unit 16 by the desired section thickness, thereby also moving the sample through the corresponding distance.

Examples of materials that may be used for the piezoelectric elements 54 include piezoelectric ceramics or piezoelectric crystals.

A linear encoder 60 is mounted on guide member 42. A linear scale 62 is provided on carriage 40 at a corresponding location. This scale can be read by linear encoder 60. Thus, the relative distance traveled between guide member 42 and carriage 40 can be detected in a simple manner, which allows the feed movement to be controlled and/or regulated in a controlled manner.

The linear scale is in particular in the form of a graduation and/or a rule.

In an alternative embodiment of the present invention, stator 52 may be mounted on carriage 40 and runner 56 may be mounted on guide member 42.

Moreover, alternatively, sample holder 12 may be stationary and cutting unit 16 may be moved relative thereto by a corresponding feed motion drive unit having a piezoelectric linear actuator 50.

What is claimed is:

1. A microtome for cutting thin sections, comprising:
   a sample holder (12) for receiving a sample to be microtomed,
   a cutting unit (16) for cutting the sample, and
   a piezoelectric linear actuator (50) for producing a feed movement between the sample holder (12) and the cutting unit (16) for setting the thickness of the sample sections,
   wherein the piezoelectric linear actuator (50) includes a stator (52) and a runner (56) which is connected to the stator (52) via at least one piezoelectric element (54) and is movable relative to the at least one piezoelectric element (54);
   the at least one piezoelectric element (54) is attached to the stator (52); and
   the at least one piezoelectric element (54) changes shape when energized such that the runner (56) is linearly moved by contact of the runner (56) with the at least one piezoelectric element (54) relative to the stator (52).

2. The microtome (10) as recited in claim 1, wherein the piezoelectric element (54) includes a piezoelectric ceramic and/or a piezoelectric crystal.

3. The microtome (10) as recited in claim 1, further comprising a control unit (23), wherein the control unit energizes the piezoelectric element (54) such that the piezoelectric element (54) moves the runner (56) linearly according to a preset sequence of movements.

4. The microtome (10) as recited in claim 1, wherein the cutting unit (16) is stationary and the sample holder (12) is movable relative to the cutting unit (16) by the piezoelectric linear actuator (50).

5. The microtome (10) as recited in claim 4, wherein the sample holder (12) is fixedly connected to the runner (56) of the piezoelectric linear actuator (50).

6. The microtome (10) as recited in claim 5, further comprising a guide member (42) extending along a longitudinal axis and a carriage (40) mounted on the guide member (42) such that the carriage (40) is movable along the longitudinal axis of the guide member (42), wherein the sample holder (12) is attached to the carriage (40).

7. The microtome (10) as recited in claim 6, wherein the runner (56) is attached to the carriage (40) and the stator (52) is attached to the guide member (42).

8. The microtome (10) as recited in claim 6, wherein the runner (56) is attached to the guide member (42) and the stator (52) is attached to the carriage (40).

9. The microtome (10) as recited in claim 7, wherein the guide member (42) is a rail.

10. The microtome (10) as recited in claim 8, wherein the guide member (42) is a rail.

11. The microtome (10) as recited in claim 6, wherein the guide member (42) is mounted on a further carriage (44) which can be moved by a further drive unit (22); and the further carriage (44) can be moved by the further drive unit (22) in such a way that the further drive unit (22) can cause the sample holder (12) to perform a reciprocating movement relative to the cutting unit (16) to cut the samples to be microtomed.

12. The microtome (10) as recited in claim 1, further comprising a sensor (60, 62) for detecting the travel of the piezoelectric linear actuator (50).

13. The microtome (10) as recited in claim 6, further comprising a sensor (60, 62) for detecting the travel of the piezoelectric linear actuator (50), wherein the sensor includes a linear encoder (60) attached to the guide member (42) and a scale (62) provided on the carriage (40).

14. The microtome (10) as recited claim 1, further comprising a control unit (23) for controlling the piezoelectric linear actuator (50); and wherein after a thin section is cut, the control unit (23) controls the piezoelectric linear actuator (50) such that the piezoelectric linear actuator (50) performs a feed movement through a preset distance.

15. The microtome (10) as recited in claim 14, further comprising an operator control unit (25) which enables setting of the preset distance and/or a speed at which the sample holder (12) and the cutting element (16) are moved relative to each other.

16. The microtome (10) as recited in claim 15, wherein the operator control unit (25) enables manual setting of the preset distance and/or a speed at which the sample holder (12) and the cutting element are moved relative to each other.

* * * * *